United States Patent [19]

McClenahan

[11] Patent Number: 5,603,335
[45] Date of Patent: Feb. 18, 1997

[54] INTRAURETHRAL CONTRACEPTIVE DEVICE

[76] Inventor: R. William McClenahan, 450 Cola Ballena, Apt. G, Alameda, Calif. 94501

[21] Appl. No.: 534,553

[22] Filed: Sep. 27, 1995

[51] Int. Cl.⁶ .................................. A61F 6/04; A61F 5/44
[52] U.S. Cl. ............................................ 128/844; 604/349
[58] Field of Search ........................... 604/349; 128/842, 128/843, 844, 918

[56] References Cited

U.S. PATENT DOCUMENTS

| | | | |
|---|---|---|---|
| 2,291,191 | 7/1942 | Scudder, Jr. | 128/294 |
| 2,696,209 | 12/1954 | Varaney | 128/842 |
| 3,373,746 | 3/1968 | White | 128/844 |
| 3,463,141 | 8/1969 | Mozolf | 128/1 |
| 3,709,220 | 1/1973 | Boyden | 128/842 |
| 4,183,358 | 1/1980 | Cohen | 604/328 |
| 4,475,910 | 9/1984 | Conway et al. | 604/349 |

FOREIGN PATENT DOCUMENTS 0204392  11/1908  Germany .

*Primary Examiner*—Robert A. H. Clarke
*Assistant Examiner*—David J. Cho

[57] ABSTRACT

A male inboard contraceptive device of the containment type including a urethral sealing member in the form of an oblong ring (1) designed to reside in a fossa navicularis (14) and engage an orificium externum (15) in a sealing relationship, it being of such outside diameter and thickness as to allow it to enter into the orifice in one axis and seal it in another: an attached flexible container bag (2) designed to reside alongside a penile shaft (12) during coitus: a tail (4) or other tensioning means attached to the bag, to regulate position of the device.

1 Claim, 3 Drawing Sheets

INTRAURETHRAL CONTRACEPTIVE DEVICE

FIELD OF INVENTION

This invention relates to a contraceptive device, and more particularly to a contraceptive device for men.

BACKGROUND—DESCRIPTION OF PRIOR ART

Over the years, several mechanical and oral products have been introduced for birth control, prophylactic condoms being one of them. However, today, condoms present the only means of protection—albeit, incomplete protection—against venereal disease a.k.a., sexually transmitted diseases (STDs) in risky (extramarital) sexual activity. Among those who engage in such sexual activity, many choose not to take this precaution. Reasons why this might be so could include cost, discomfort, dissatisfaction, unavailability. I believe dissatisfaction would predominate. It is widely known that wearing a "rubber" is regarded as obligatory, and not as a natural prelude to pleasure. Condoms introduce a barrier to intimate genital contact.

U.S. Pat. No. 4,183,358 to Cohen (1980) discloses a contraceptive device that appears to solve the problem of loss of genital skin contact, but has some disturbing aspects. For example, a tube of undescribed rigidity is inserted somewhat far into a male member, after which a rigid cap covering the glans is threaded thereon. U.S. Pat. No. 2,291,191 to Scudder (1942) employs a lengthy and narrow passageway restricting fluid flow, and protrudes rigidly externally.

SUMMARY OF THE INVENTION

The invention is an inboard or intraurethral contraceptive device for males consisting of an anchoring and sealing ring and a flexible container bag worn extending outside the urethra, and affixed atop a penile shaft, with the flexible bag held in place by an adhesive strip or an elastic loop.

Accordingly, one object and advantage of the present invention is possible superior pleasure during sexual intercourse over current-day external contraceptive appliances. A common complaint of conventional condoms is that feeling is disguised or lacking in intensity. Considering dissatisfaction, here is an offering into the marketplace of an appliance that, by my reckoning, provides 70 percent to 80 percent of the genital skin contact present in ordinary coitus contrasted with that provided by condoms offering no genital skin contact. This opens a door for many couples currently practicing "unprotected" intercourse, and leaves open a market opportunity for cross-over condom users who have more concern for preventing conception than for preventing disease.

My invention relies on a little-discussed physiological feature inside normal intact males. Slightly inside an external urethra opening lies a restriction (i.e., a nozzle of sorts,) in one reference called an external urethral orifice (*Functional Human Anatomy*—Crouch, 1978) or otherwise referred to as an orificium externum (Scudder), whose diameter is significantly smaller than the rest of the urethra, and which immediately leads to an enlarged chamber medically known as the fossa navicularis.

In conjunction with this membrane, I use the solid geometric theorem of shrinking circumferences as a ring or coin is rotated edge-on to an observer. A ring can pass through a smaller diameter flexible band once that ring has been rotated ninety degrees, as long as the ring's edge is sufficiently narrow. The flex band will contort around the ring to essentially encompass the ring, and allow it to emerge on the other side. Subsequently, as the ring is turned to a coincident axis with the flexible band, the ring is now too large to be passed back through. So is the case of passing a rigid or semi-rigid ring-shaped appliance edge-first through an orifice of the human body. Beyond the orifice, in a larger diameter cavity, the ring is returned to coincident axis with the orifice, thus locking it in place, and establishing a sealing relationship. Additionally, when the ring is widened or made oblong, and inserted by way of the short axis, a substantially larger resistant surface to removal can be obtained.

An attached flexible containment bag extending outside the body and a connecting "tail" of the same flexible material is meant to be routed over the top of the glans penis and atop the dorsal side of the penile shaft. Together, they should be held in place with the use of a pre-attached adhesive strip or an elastic loop. Keeping the bag in a relatively fixed position would serve to neither unduly flex the bag, nor tug at the orifical connection. Coitus would then be conducted in the usual manner, with the bag containing all eventual semen, and at the same time—as an adjunct—there would be offered no direct path for vaginal infection into the male urethra.

The present invention should not be as invasive to the wearer nor his participant as that proposed by Cohen, and should not be as difficult to make. Mine contains no switching or expanding mechanisms, but instead, makes use of a theorem of solid geometry not contemplated by the Cohen or Scudder devices.

As to safety and efficacy, the present invention has very high promise. A non-working magnified model of the present invention has been sculpted in clay.

Other objects and advantages of the present invention should become apparent from consideration of the drawings and description.

DETAILED DESCRIPTION OF INVENTION

The present invention includes, firstly, an oblong ring or oblong annular member assuming a toroidal shape on its outermost surface. A radial facing edge is designed to be sufficiently wide so as not to irritate the surrounding tissues during movement. A breech side or posterior face of the ring is rounded, continuing toward a central hole, which begins as a sizable bore and decreases in diameter approaching an anterior sealing face. The resulting bore is the approximate diameter of an external urethral orifice.

A flexible container bag or flexible container means of varied bore is bonded to the bore of the ring axially so as to form a moisture-proof seal.

Figure 2A:
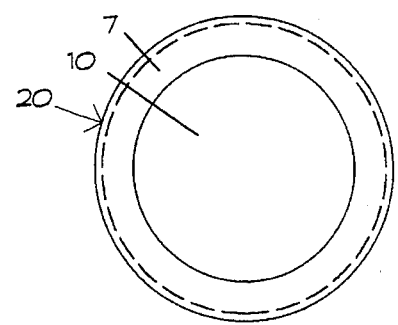
FIG. 2A is a front view of a regular ring detail.
Figure 2B:
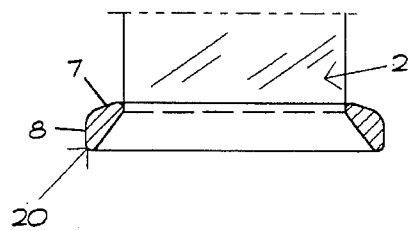
FIG. 2B is a cross-section edge view of the ring in FIG. 2A.

Referring to the drawings, FIGS. 2A and 2B present one embodiment of the invention. In this case, an annular member or ring 20 is bonded within the bore 10 or posterior face to a flexible container bag 2 with the bag emerging on a narrow-bore anterior side of the ring.

Figure 1B:
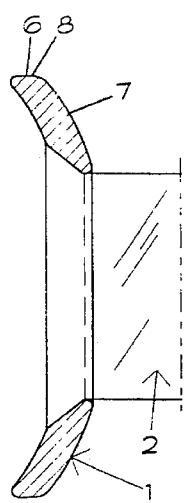
FIG. 1B is a cross-section edge view of the ring in FIG. 1A showing a portion of a flexible container bag bonded to the ring.
Figure 1A:
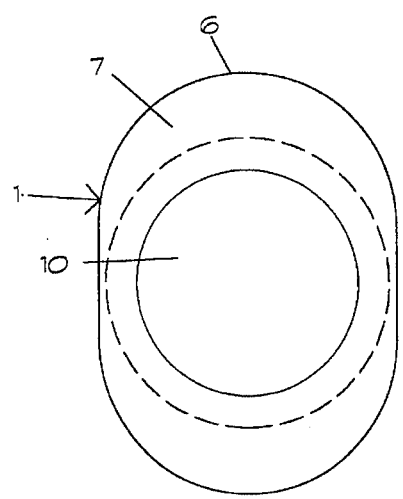
FIG. 1A is a front view of an oblong ring detail.
Figure 1C:
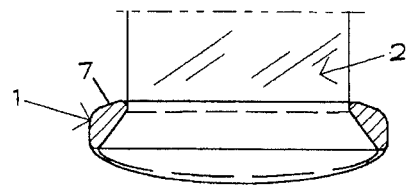
FIG. 1C is a cross-section edge view of the same ring in FIG. 1A from a different perspective.

FIGS. 1A, 1B and 1C depict another embodiment detail of the present invention. In this embodiment, an oblong ring or oblong annular member 1 substitutes for the ring 20 in FIGS. 2. Ring 1 renders an arcuate shape when viewed from top edge. Further, this yields a vastly increased surface area of anterior sealing face 7. A flexible container bag is similarly bonded to the oblong ring 1 as was described for FIGS. 2A and 2B. FIG. 1A is an axial view detail of oblong ring. FIG. 1B is a cross-sectional edge view detail along the elongated axis, showing a portion of emerging container bag 2. FIG. 1C is a cross-sectional edge view detail along the short axis.

Figure 3:
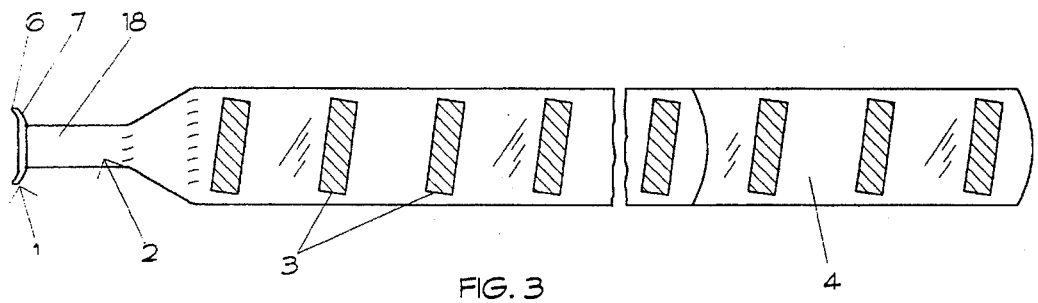
FIG. 3 is a top view of an oblong embodiment of the complete present invention showing an attached flexible container bag.
Figure 4:
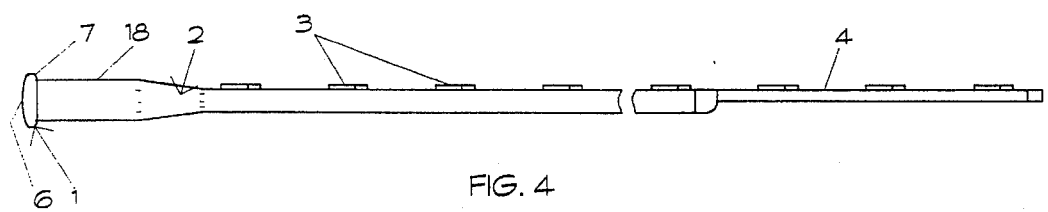
FIG. 4 is an edge view of the complete invention shown in FIG. 3.

FIGS. 3 and 4 more clearly depict the size and shape of the container bag 2 and its proportion to sealing ring. The views are respectively, a top view of oblong ring embodiment and an edge view of the same embodiment. A narrow neck 18 portion of container bag permits sharp bending, so as to facilitate insertion and removal of the invention. A distal length of container bag is broader, flatter, and is populated on one flat side with adhesive strips or by one continuous adhesive strip throughout its length. Lastly, the container bag may extend into a tail 4 of similar or identical material to an equivalent length of container bag without a tail. Extension tail 4 is a variation of full-length container bag. The full length is probably necessary for positional regulation or stability or the annular member 1 or 20 during use.

Figure 5:
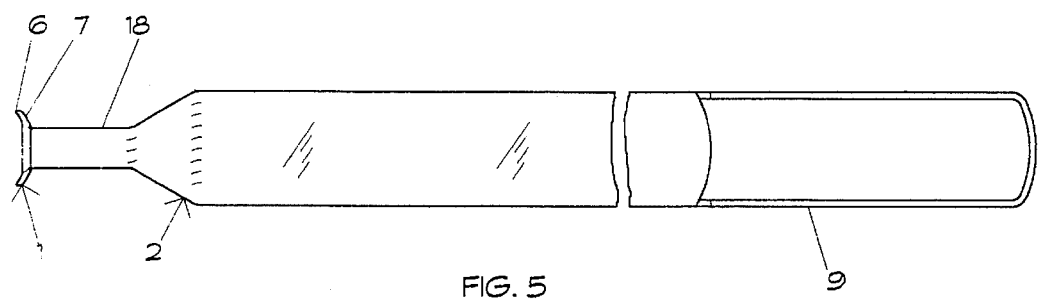
FIG. 5 is a top view of an embodiment having an elastic loop.
Figure 6:
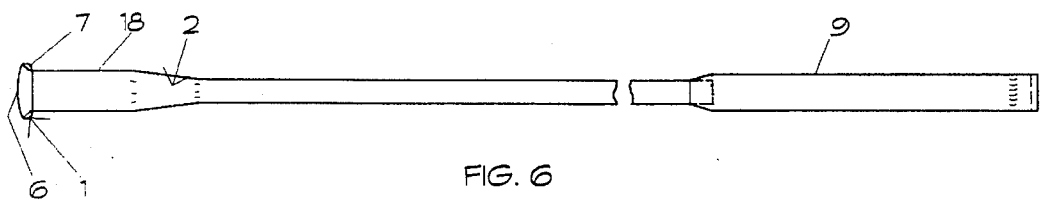
FIG. 6 is an edge view of the embodiment having an elastic loop.

FIGS. 5 and 6 show a top view and an edge view of an embodiment of the present invention where an extension tail has been replaced by an elastic loop.

OPERATION OF INVENTION

The intraurethral contraceptive device is anticipated to be packaged with a small quantity of lubricant and a throwaway inserter tool. The manner of using the device differs from conventional condoms, in that a nominal portion of it is inserted into the male human body.

A wearer must first establish proper fit. A quantity of lubricant is applied to the edges of oblong ring 1 or ring 20 and to approximately 1 cm of the outside of narrow neck 18. The invention is laid flat on a table with distal end of container bag 2 or of tail 4 or of elastic loop 9 away from the wearer, and with adhesive strips 3 facing up. One of two short axis edges 6 of oblong ring 1 is gently worked into an external urethra opening 16 of wearer, with the wearer observing the long axis edge of ring from above. An inserter tool 5 is used to continue to push ring with attached container bag beyond view.

From this point, ring 1 should be able to slide inward past an external urethral orifice or orificium externum 15 by pinching front and back (dorsal and ventral surfaces) of a glans penis 11 with the thumb and forefinger until ring passes into an enlarged chamber of the urethra 17 medically known as the fossa navicularis 14. Following this, a slight tugging on the exposed container bag 2 will right the ring, i.e., cause it to be tilted ninety degrees into its wearing position. Ring 1 will thus lie with its axis coincident to the axis of the bore of the urethra. With its consequent circumference considerably larger than that of external urethral orifice 15, ring 1 will strongly resist removal by pulling. The exposed distal end of container bag 2 outside the wearer's body is, at this point, loosely lain upon a dry and erect penis surface 12 beginning upwardly across glans penis 11, and then rearward toward the pubic area on dorsal side of the penis. Sticky adhesive strip or adhesive strips 3 will then hold the flexible bag 2 against the penis surface in an operating position. Narrow neck or tubular-shaped portion 18 of container bag 2 coming out should not be twisted.

Using the elastic loop 9 embodiment (FIGS. 5 and 6,) the loop is expanded with both hands, and brought rearward toward the base of penis 12, ensuring that the container bag 2 remains smoothly across the top, and then relaxing the loop around penis shaft. Loop 9 may, in fact, have to be turned wrong-side-out before installing around penis 12 shaft. An outside surface of exposed container bag 2 may be lubricated as required.

Figure 7:
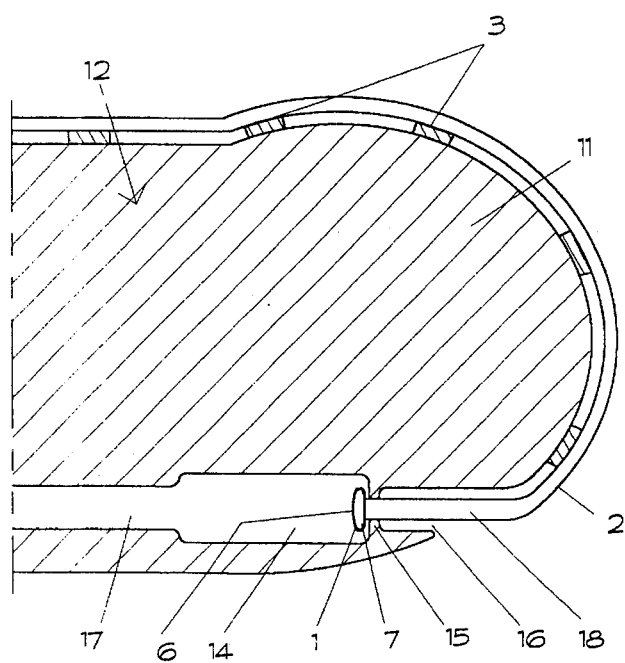
FIG. 7 is a schematic of the intraurethral contraceptive device as it would look when properly worn.
Figure 8:
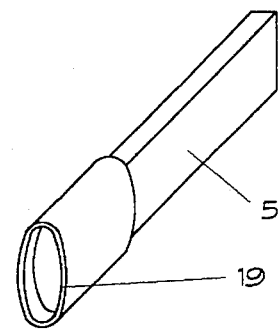
FIG. 8 shows a possible insertion tool including a handle 5 and an inserter hollow face 19.

FIG. 7 is a schematic depiction of the invention as it should look when properly installed on a wearer. Posterior-facing short axis edges 6 of ring 1 can be seen to be extending backward, providing a smooth sealing edge 7 against external urethral orifice 15. It is depicted comfortably ensconced within fossa navicularis 14, but prevented from removal by membrane of external urethral orifice. Snugness of narrow neck 18 as container bag 2 is draped over glans penis 11 and secured by adhesive strips 3 will serve to keep rocking motion from dislodging or tipping ring 1. Thus the container bag is positioned to receive eventual erupting semen, and fulfill its function as a contraceptive.

The invention is removed by squeezing the penis 12 immediately outside the location of the ring 1 front-to-back, causing the ring to tilt, and to no longer be in coincident axis with the urethra 17, thereby making the short axis of the ring susceptible to removal by pulling. Container bag 2 in gently pulled until the entire device slides out. "Soft" adhesive 3 permits easy removal of container bag 2 from skin of penis 12.

Consequence of disposal has not been studied.

CONCLUSION, RAMIFICATIONS AND SCOPE OF INVENTION

Thus the reader can see that the intraurethral contraceptive device provides a promising economical solution for a corner of the adult consumer market unpleased with the present-day contraceptive choices.

While my above description contains many specificities, these should not be construed as limitations on the scope of the present invention, but rather as an exemplification of one preferred embodiment thereof. Other variations are possible. For example a ring can be made of a rigid material, but could conceivably be made of a semi-rigid material, instead. Its internal void could be somewhat non-annular, i.e., made eleven-sided or oval, but still be covered under the scope of this application. This applies to the outside shape, as well. The flexible container bag could be extended to act as a tail, and the tail thereby eliminated, while still being covered. Tail could be made elastic, and hold distal end of container bag in place by surrounding penile shaft much as does a rubber band. The convenient adhesive strips on one side of the container bag and the tail could be substituted by an adhesive gel applied at time of use. The inserter tool drawing is for illustration, only, and is not an integral part of this application, nor does its absence prevent the present invention from being used.

Although the invention has been described with references to a particular embodiment, it is to be understood that this embodiment is merely illustrative of the application of the principles of the invention. Numerous modifications may be made therein and other arrangements may be devised without departing from the spirit and scope of the invention.

I claim:

1. A male intraurethral contraceptive device comprising:
   (a) a urethral sealing member selected from the group consisting of rounds and oblong rings, adapted to be received in a urethra in a perpendicular axis as defined by the urethra, said ring having a central bore permitting the passage of semen, and
   (b) a flexible, elongated hollow container means attached to said ring and emanating from the bore of said ring and extending outside the urethra, said container means having sufficient length to allow affixation to a penis shaft whereby said ring, being brought into a coincident axis with the urethra bore, the sealing member along with said container means serve to hold said ring in a position within a fossa navicularis to effect a sealing relationship between said ring and the orificium externum, wherein the container means further comprises,
   an adhesive means applied to a portion of one outside surface of said container means to engage the penis shaft in a holding relationship, or
   an elastic loop attached to a distal end of said container means to engage the penis shaft in a holding relationship.

* * * * *